(12) United States Patent
Testa

(10) Patent No.: US 11,266,493 B2
(45) Date of Patent: Mar. 8, 2022

(54) EYELID SUPPORTERS AND RELATED METHODS

(71) Applicant: Nicholas Testa, Corvalis, OR (US)

(72) Inventor: Nicholas Testa, Corvalis, OR (US)

(73) Assignee: Nicholas Testa, Corvallis, OR (US)

(*) Notice: Subject to any disclaimer, the term of this patent is extended or adjusted under 35 U.S.C. 154(b) by 863 days.

(21) Appl. No.: 15/737,056

(22) PCT Filed: Jun. 16, 2016

(86) PCT No.: PCT/US2016/037852
§ 371 (c)(1),
(2) Date: Dec. 15, 2017

(87) PCT Pub. No.: WO2016/205499
PCT Pub. Date: Dec. 22, 2016

(65) Prior Publication Data
US 2018/0168799 A1     Jun. 21, 2018

Related U.S. Application Data

(60) Provisional application No. 62/181,383, filed on Jun. 18, 2015.

(51) Int. Cl.
*A61F 2/14* (2006.01)
*A61F 9/007* (2006.01)
(Continued)

(52) U.S. Cl.
CPC .............. *A61F 2/14* (2013.01); *A61F 9/00* (2013.01); *A61F 9/00718* (2013.01); *A61F 2/0059* (2013.01); *A61F 2250/0007* (2013.01)

(58) Field of Classification Search
CPC ........ A61F 2/14; A61F 9/007; A61F 9/00718; A61F 2/0059
See application file for complete search history.

(56) References Cited

U.S. PATENT DOCUMENTS 3,710,788 A    1/1973  Reeves
5,522,889 A *  6/1996  Baker ................. A61F 9/00718
                                                      128/898
(Continued)

FOREIGN PATENT DOCUMENTS

DE         431950 C       7/1926
JP      2003533326 A     11/2003
(Continued)

OTHER PUBLICATIONS

PCT/US2016/037852, International Search Report and Written Opinion, dated Sep. 7, 2016, 15 pages.
(Continued)

*Primary Examiner* — William H Matthews
(74) *Attorney, Agent, or Firm* — Stoel Rives LLP

(57) ABSTRACT

An assembly for lifting a lower eyelid can be surgically implanted into a patient. The assembly can include a mounting plate, an eyelid support member, and an elongate shaft that extends between and couples the mounting plate to the eyelid support member. The mounting plate can be coupled to facial bone, such as the zygomatic bone, while the eyelid support member contacts and lifts up an inferior tarsus and the lower eyelid of the patient.

14 Claims, 19 Drawing Sheets

(51) Int. Cl.
 *A61F 9/00* (2006.01)
 *A61F 2/00* (2006.01)

(56) References Cited

U.S. PATENT DOCUMENTS

| | | |
|---|---|---|
| 5,843,147 A | 12/1998 | Testerman et al. |
| 2002/0040225 A1 | 4/2002 | Sellers et al. |
| 2004/0210225 A1 | 10/2004 | Amis |
| 2005/0256526 A1 | 11/2005 | Johnston |
| 2007/0037120 A1 | 2/2007 | Ritter |
| 2007/0156143 A1 | 7/2007 | Lancial |
| 2008/0200993 A1 | 8/2008 | Henderson |
| 2008/0281327 A1 | 11/2008 | Helfteren |
| 2012/0109292 A1 | 5/2012 | Barbosa |
| 2013/0158607 A1 | 6/2013 | Rabiner et al. |
| 2015/0105858 A1 | 4/2015 | Papay et al. |

FOREIGN PATENT DOCUMENTS

| | | |
|---|---|---|
| JP | 2005040250 A | 2/2005 |
| JP | 2008284348 A | 11/2008 |
| WO | 2001089392 A2 | 11/2001 |
| WO | 2009091802 A2 | 7/2009 |

OTHER PUBLICATIONS 16812428.7, European Search Report, dated Mar. 14, 2019, 5 pages.
PCT/US2016/037852, International Preliminary Report on Patentability, dated Dec. 29, 2017, 8 pages.

\* cited by examiner

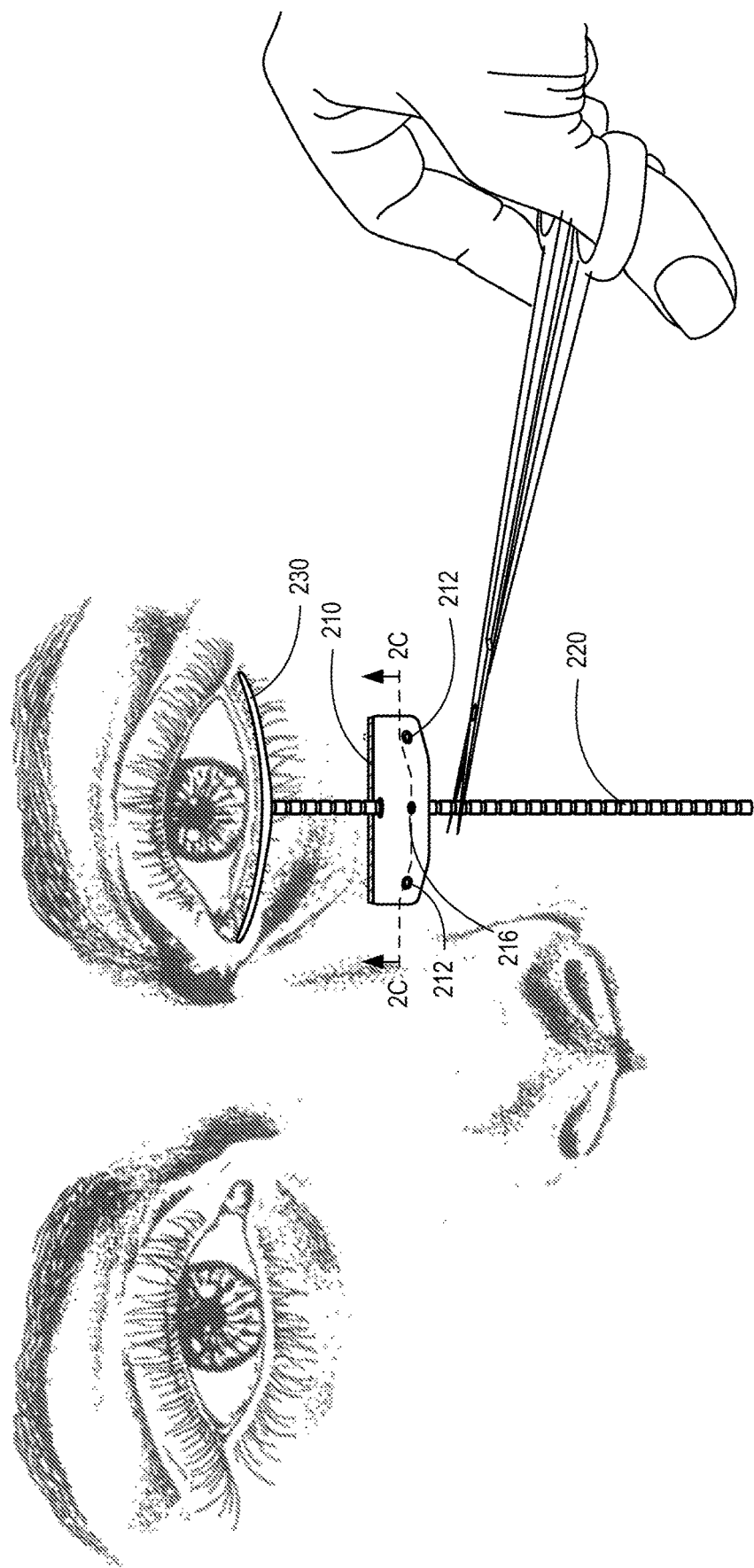

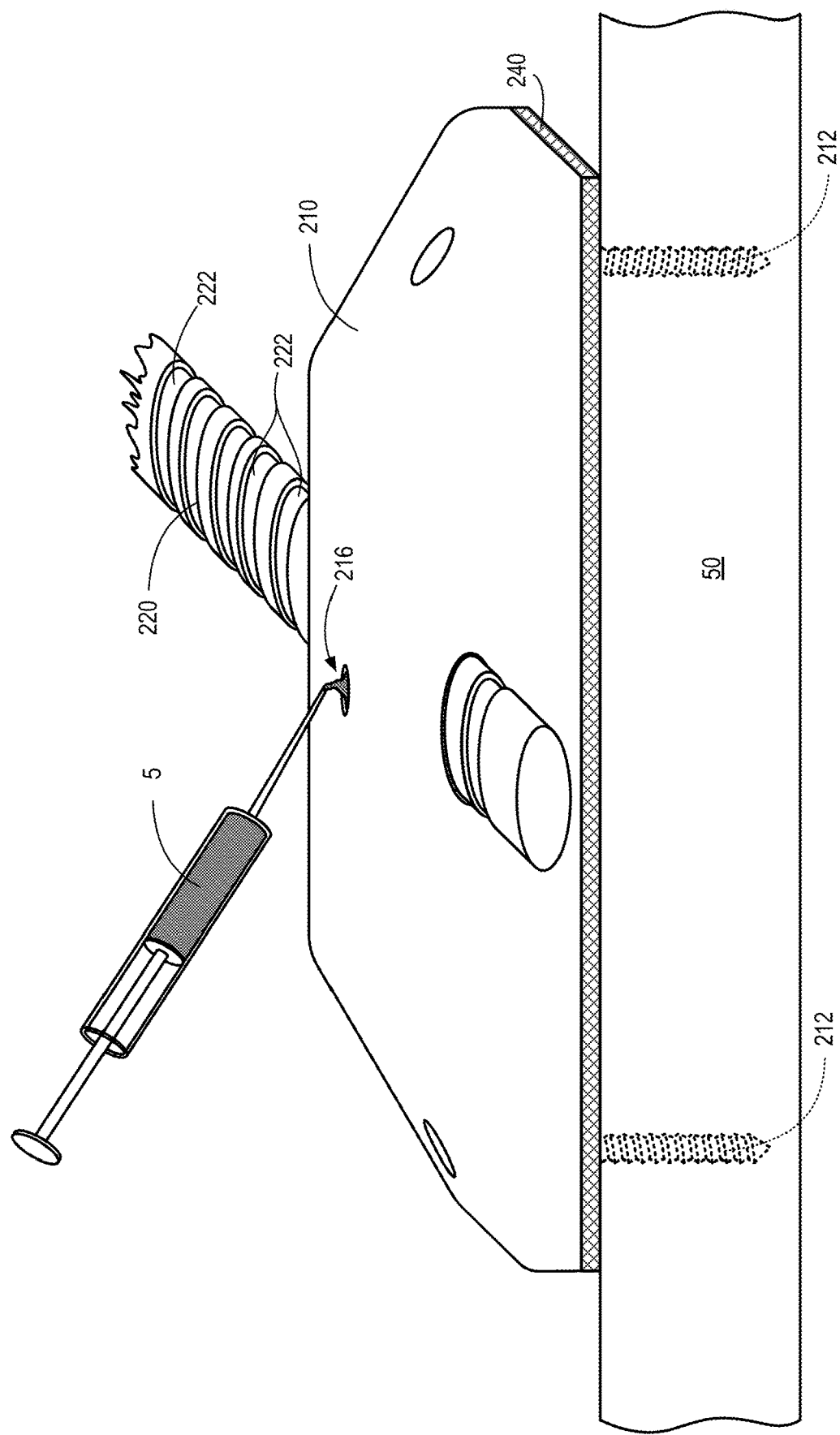

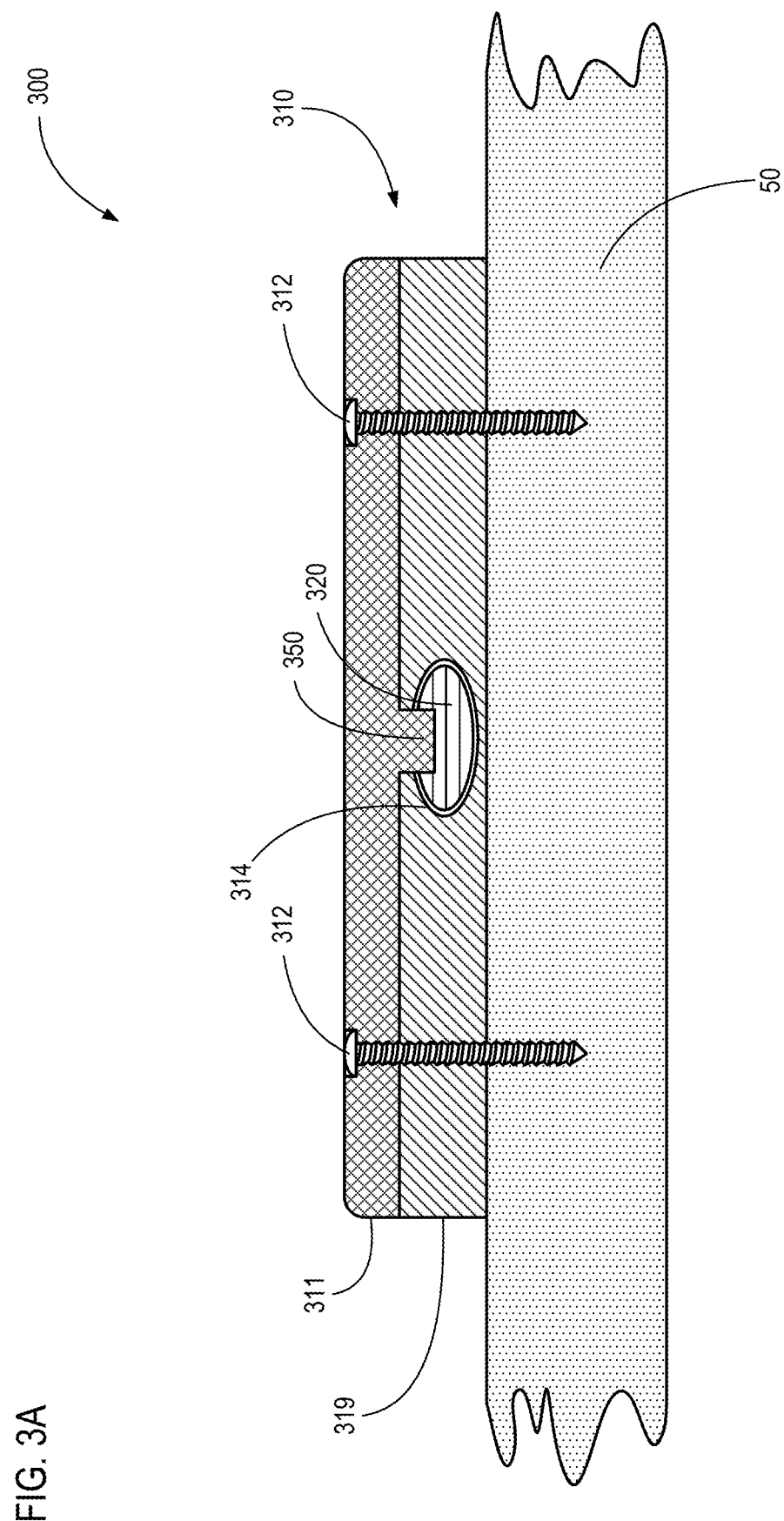

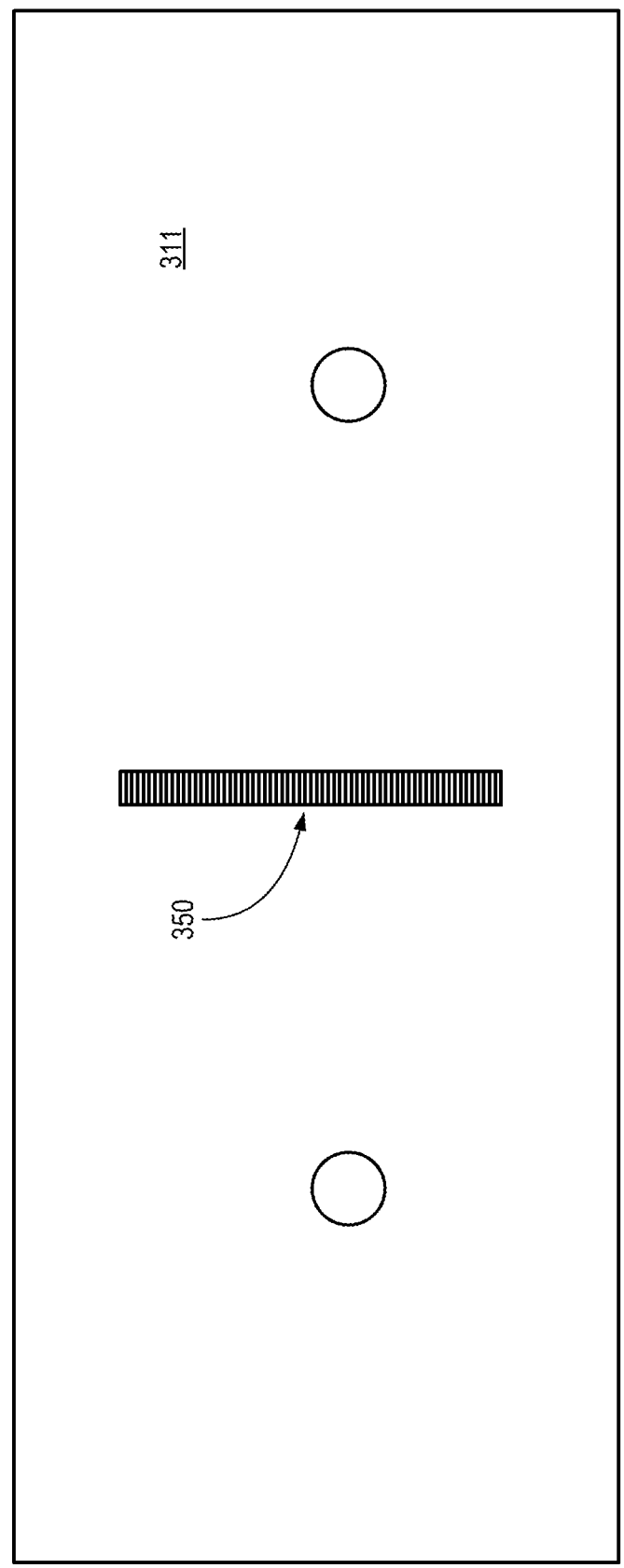

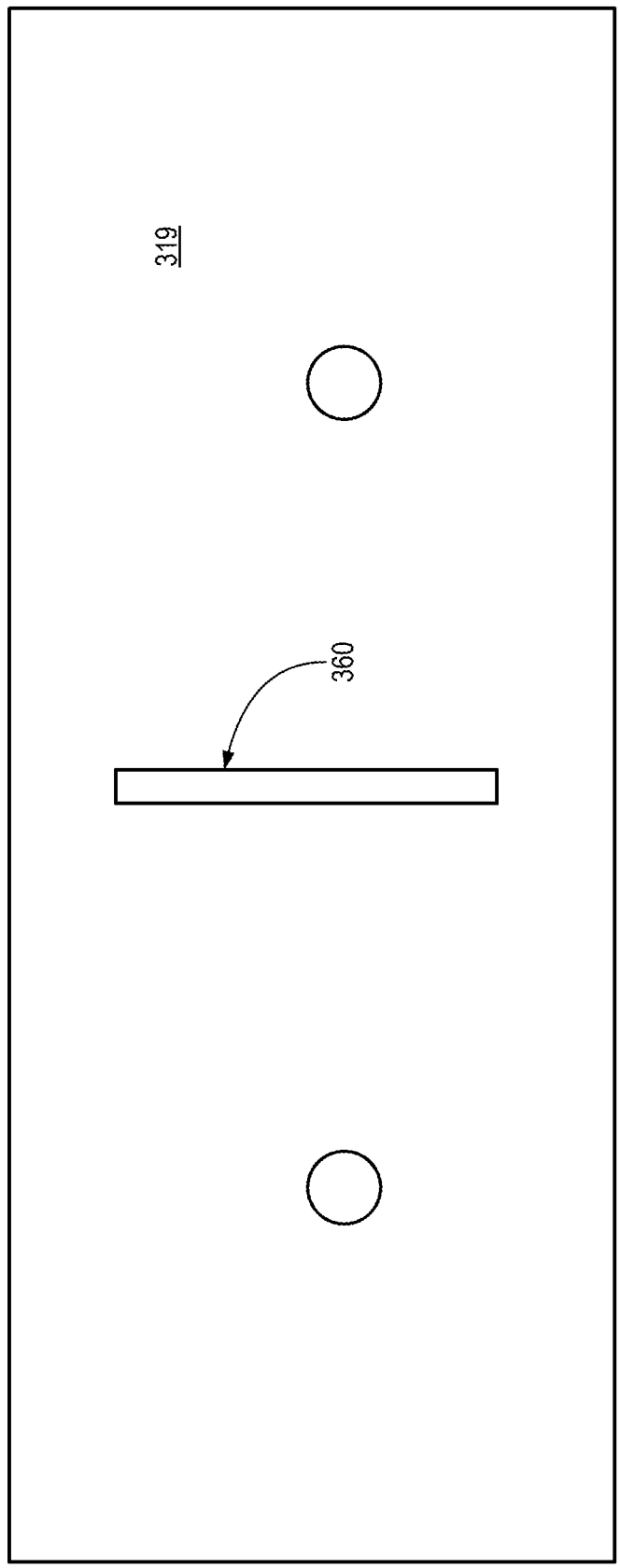

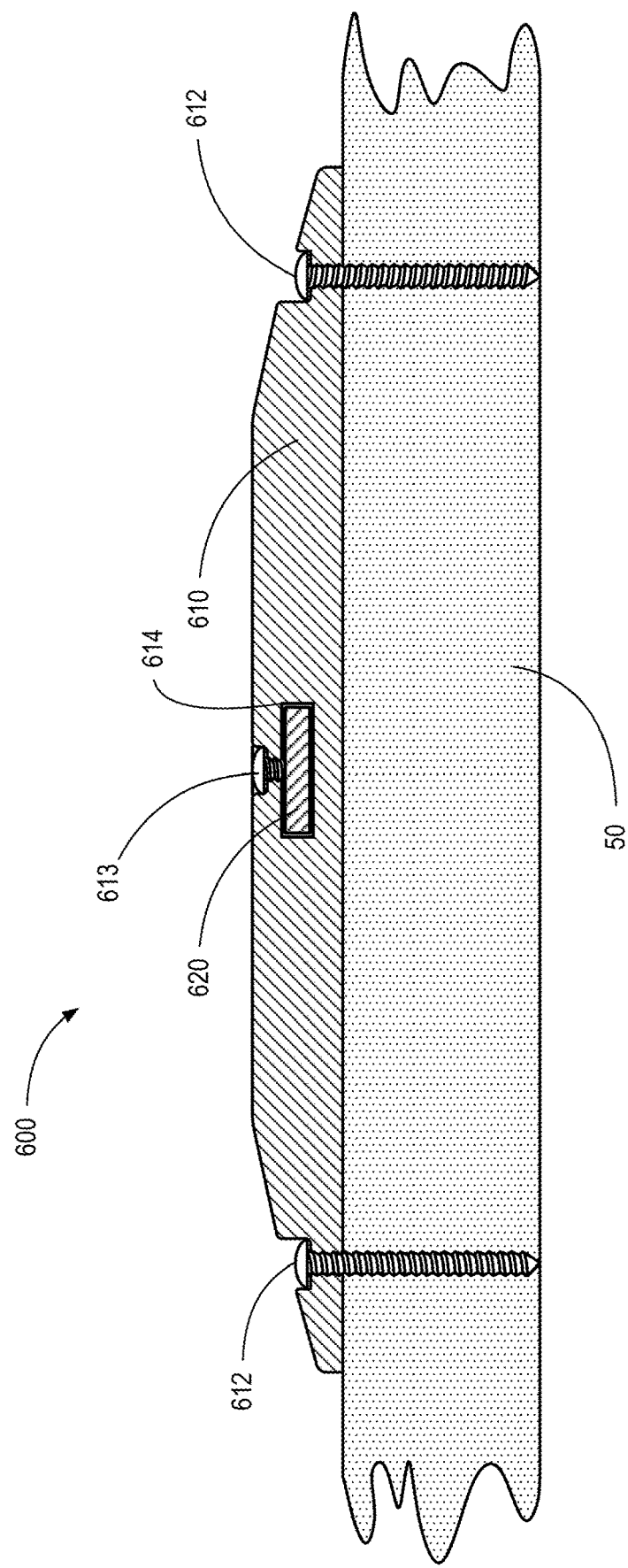

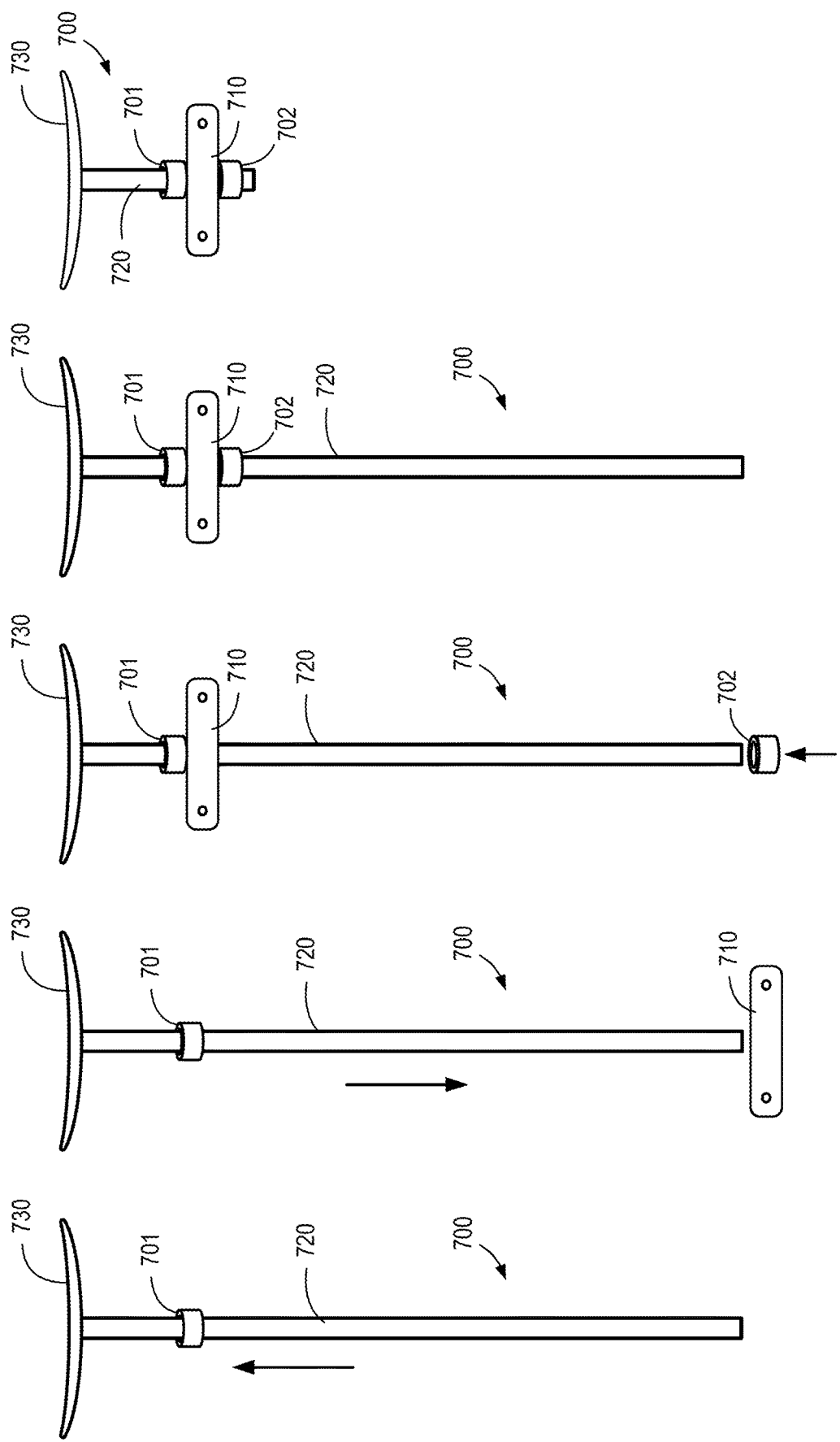

EYELID SUPPORTERS AND RELATED METHODS

RELATED CASES

This application is the United States National Stage of International Application No. PCT/US16/37852, filed Jun. 16, 2016 which claims priority to U.S. Provisional Application No. 62/181,383 titled "EYELID SUPPORTERS AND RELATED METHODS" and filed on Jun. 18, 2015, both of which are hereby incorporated by reference in their entirety.

TECHNICAL FIELD

The present disclosure relates generally to the field of medical devices, such as medical devices for supporting a lower eyelid.

BACKGROUND

Lower eyelid paralysis affects tens of thousands of people worldwide. Similar conditions may also affect other mammals, such as dogs. Paralysis of the lower eyelid may result in ectropion, lid laxity, epiphora, lagophthalmos, and/or corneal damage. Corrective measures for lower eyelid paralysis include surgical reconstruction and/or implantation of lower eyelid spacers to stabilize and support lower eyelids. However, existing devices and methods for treating lower eyelid paralysis suffer from one or more drawbacks or may perform less than optimally in one or more respects. Certain embodiments disclosed herein can address one or more of these issues.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2B is a front view of the eyelid support assembly of FIG. 2A, depicting the cutting off of a bottom portion of the elongate shaft.

FIG. 2D is a perspective view of a portion of the eyelid support assembly of FIG. 2A, depicting delivery of an adhesive to fasten the elongate shaft to the mounting plate.

FIG. 3A is a cross-sectional view of an eyelid support assembly with a mounting plate that has a first portion and a second portion.

FIG. 3B is a bottom view of the first portion of the mounting plate of FIG. 3A.

FIG. 3C is a top view of the second portion of the mounting plate of FIG. 3A.

FIG. 6 is a cross-sectional view of an eyelid support assembly according to another embodiment.

FIG. 7A is a front view of components of an eyelid support assembly in a first configuration.

FIG. 7B is a front view of components of the eyelid support assembly of FIG. 7A in a second configuration.

FIG. 7C is a front view of components of the eyelid support assembly of FIG. 7A-7B in a third configuration.

FIG. 7D is a front view of components of the eyelid support assembly of FIG. 7A-7C in a fourth configuration.

FIG. 7E is a front view of components of the eyelid support assembly of FIG. 7A-7D in a fifth configuration.

DETAILED DESCRIPTION

Figure 1A:
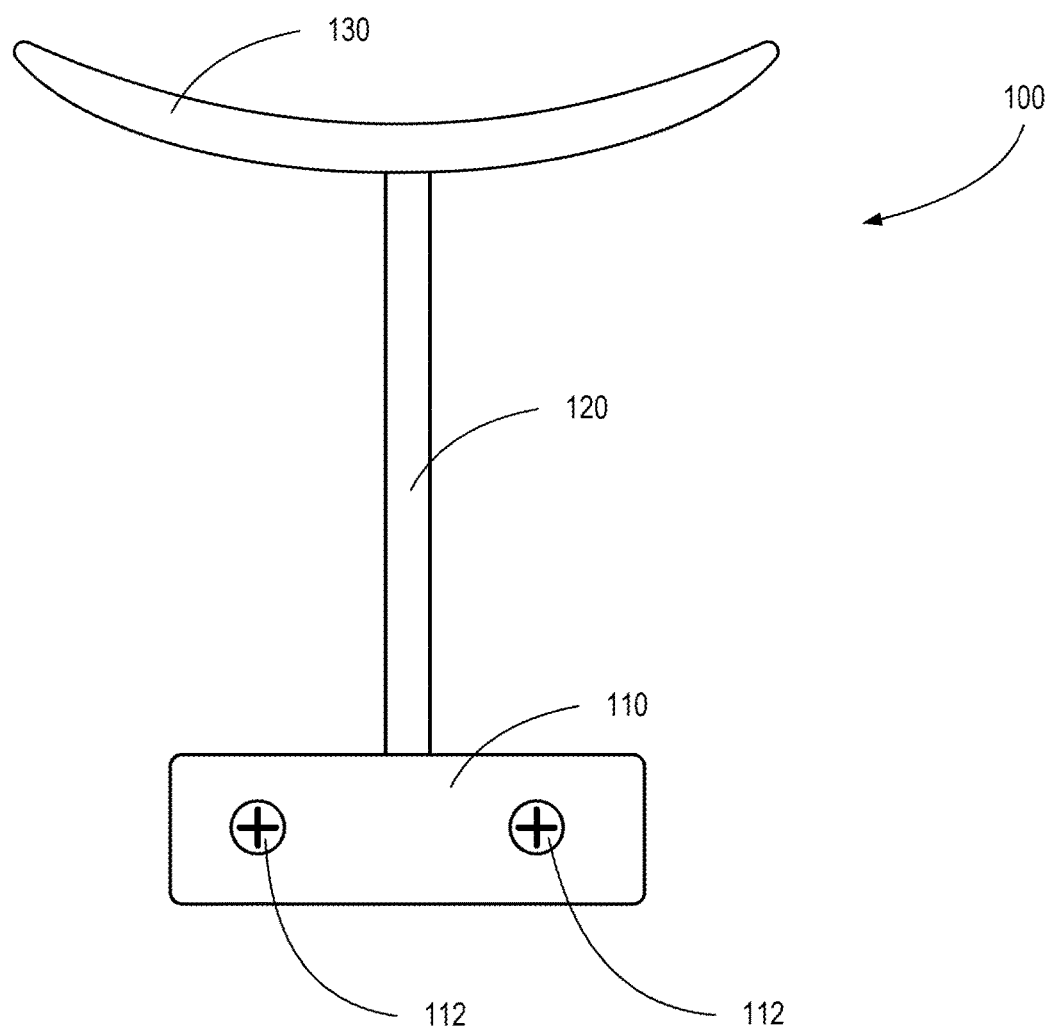
FIG. 1A is a front view of an eyelid support assembly.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in the drawings, the drawings are not necessarily drawn to scale unless specifically indicated.

The phrases "connected to" and "coupled to" are used in their ordinary sense, and are broad enough to refer to any suitable coupling or other form of interaction between two or more entities, including mechanical, frictional, compression, fluid and thermal interaction. Two components may be coupled to each other even though they are not in direct contact with each other. For example, a first component may be coupled to a second component through a third component. The phrases "attached to" or "attached directly to" refer to interaction between two or more entities which are in direct contact with each other and/or are separated from each other only by a fastener of any suitable variety (e.g., screws, compression screws, compression bars, clamps, crimping beads, or an adhesive). The term patient is broad enough to include both human and other non-human mammalian patients.

Many humans and other mammals suffer from lower eyelid paralysis or other conditions that afflict a lower eyelid. Such conditions may, among other things, cause the lower eyelid to turn outward, increase the laxity of the lower eyelid, and/or impede the complete closure of the eyelids. Lower eyelid problems can also promote irritation, discomfort, infection, and/or corneal damage. Such problems may also negatively affect the cosmetic appearance of the eye region.

Eyelid support assemblies can be used to lift or otherwise support a lower eyelid. For example, in some embodiments disclosed herein, an eyelid support assembly includes a mounting plate, an elongate shaft, and an eyelid support member. The mounting plate may be attached or otherwise coupled to a facial bone (e.g., a zygomatic bone, maxilla, or other facial bone above the lower jaw) to function as a scaffold to which one or more other elements of the eyelid support assembly may be attached. For example, the elongate shaft may include a first end that is attached to a mounting plate and a second end that is attached to an eyelid support member. Stated differently, the elongate shaft may extend between and couple the mounting plate to the eyelid support member. In some embodiments, the eyelid support member is attached (e.g., sutured) to an inferior tarsus of a patient's lower eyelid. For example, the eyelid support member may be disposed beneath, attached to, and in contact with the inferior tarsus along the entire length of the inferior tarsus. Due to the attachment of the eyelid support assembly to both facial bone (through the mounting plate) and the inferior tarsus (through the eyelid support member), the eyelid support member may exert an upward and/or inward force that lifts or otherwise displaces the patient's eyelid. Such displacement may improve the position of the lower eyelid.

In some embodiments, the eyelid support assembly is integrally formed, while in other embodiments the eyelid support assembly is assembled by coupling the component parts of the eyelid support assembly to one another.

In some embodiments, a kit, such as a surgical kit, may be supplied for supporting a lower eyelid. The kit may include one or more of the following: a mounting plate, an eyelid support member, an elongate shaft, a fastener (e.g., a screw) for coupling a mounting plate to a facial bone, a fastener (e.g., a screw or crimping bead) for coupling the elongate shaft to the mounting plate, a sterilizing agent, an alignment jig, a screwdriver, a crimping tool, an adhesive, an adhesive dispenser, a box, etc. In some embodiments, the adhesive is a cyanoacrylate glue or a thermoplastic (e.g., HDPE). In some embodiments, the adhesive dispenser is a cyanoacrylate glue dispenser or a dispenser for delivering a thermoplastic (e.g., HDPE) at an elevated temperature.

In some embodiments, an eyelid support assembly may be implanted into a patient. Implanting an eyelid support assembly may involve coupling the eyelid support member to a facial bone of a patient such that the eyelid support member is positioned to lift up the inferior tarsus. For example, implanting an eyelid support assembly may involve one or more of the following steps: coupling a mounting plate to a facial bone; inserting an elongate shaft through a channel of the mounting plate; securing the elongate shaft relative to the mounting plate; attaching (e.g., suturing) an eyelid support member to an inferior tarsus (e.g., a lower portion of the inferior tarsus); etc.

Figure 1B:
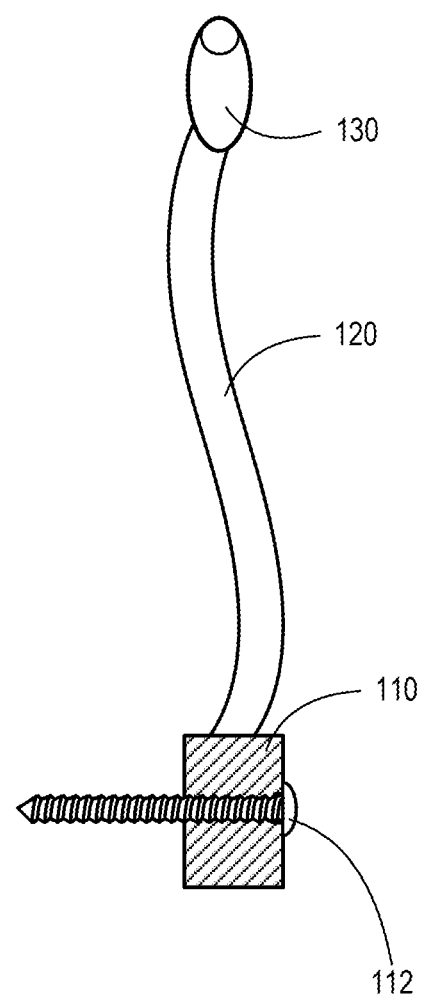
FIG. 1B is a side view of the eyelid support assembly of FIG. 1.

FIGS. 1A-1B provide alternative views of an eyelid support assembly 100 (i.e., an assembly for lifting an eyelid, such as a lower eyelid). More particularly, FIG. 1A provides a front view of the eyelid support assembly 100. FIG. 1B provides a side view of the eyelid support assembly 100. The eyelid support assembly 100 includes a mounting plate 110, an elongate shaft 120, and an eyelid support member 130.

In the embodiment depicted in FIGS. 1A and 1B, the mounting plate 110 is configured for coupling to a facial bone, such as a zygomatic bone. For example, the mounting plate 110 may be attached to a zygomatic bone via one or more fasteners 112 (e.g., bone screws). The mounting plate 110 may function as a scaffold to which one or more other elements of the eyelid support assembly 100 may be attached.

The elongate shaft 120 is configured to extend between and couple the mounting plate 110 to the eyelid support member 130. For example, in FIGS. 1A and 1B, the elongate shaft 120 is attached to both the mounting plate 110 and the eyelid support member 130, thereby coupling the mounting plate 110 to the eyelid support member 130. The elongate shaft 120 may be formed from flexible material that enables the elongate shaft 120 to follow a tortuous path, such as the path shown in FIG. 1B (see also FIG. 9). In the embodiment depicted in FIGS. 1A and 1B, the elongate shaft 120, the mounting plate 110, and/or the eyelid support member 130 are integrally formed. In other embodiments, one or more of these components are manufactured separately and subsequently attached to the remaining components via a fastener (e.g., an adhesive, welding, compressions bars, crimping beads, screws, etc.). For example, in some embodiments, the elongate shaft and the eyelid support member are integrally formed and attached to the mounting plate via a fastener.

The length of the elongate shaft 120 of the eyelid support assembly 100 may be selected to match the anatomical architecture of the patient. For example, in some patients, the distance from the zygomatic bone to the location where the bottom edge of the inferior tarsus should be located may be relatively long. In other patients, the distance from the zygomatic bone to the proper location of the inferior tarsus is relatively short. Accordingly, in some embodiments, a practitioner may select, from a variety of eyelid support assemblies of different lengths, an eyelid support assembly 100 that has an elongate shaft 120 of appropriate length to provide the proper amount of lift to an eyelid when the mounting plate 110 is secured to a facial bone of the patient.

The eyelid support member 130 may be configured to contact eyelid tissue, thereby providing lift to a paralytic eyelid. For example, in some embodiments, the eyelid support member 130 contacts and/or couples to (e.g., via sutures that wrap around or go through) a lower portion of the inferior tarsus of the patient, thereby lifting the inferior tarsus (and the lower eyelid of the patient). The eyelid support member 130 may be configured to extend horizontally to approximate the width of the lower eyelid (i.e., the full length of the inferior tarsus). In some embodiments, the eyelid support member 130 is curved (e.g., banana-shaped to follow the contour of the lower eyelid/inferior tarsus). In other embodiments, the eyelid support member may adopt a different shape.

The components of the eyelid support assembly 100 may be made from any suitable material. For example, in some embodiments, one or more of the mounting plate 110, elongate shaft 120, and eyelid support member 130 comprise or consist essentially of a biocompatible polymer, such as ultra-high molecular weight polyethylene. More particularly, in some embodiments, the mounting plate comprises or consists essentially of ultra-high molecular weight polyethylene. In some embodiments, one or more components, such as a mounting plate, comprise or consist essentially of titanium. In some embodiments, one or more of the mounting plate, the elongate shaft 120, and the eyelid support member 130 are formed from two or more different biocompatible polymers. For example, a component may be made by injecting different biocompatible polymers into a mold.

The eyelid support assembly 100 may be used to support an eyelid, such as a paralytic lower eyelid. For example, in the absence of corrective measures, a paralytic eyelid may tend to droop, causing the eyelid to be disposed at a relatively low position. The eyelid support member 130 may act on eyelid tissue, such as the inferior tarsus, thereby lifting the eyelid to a desired position. Stated differently, the eyelid support member 130 may exert a force that causes the eyelid to be disposed higher than it would be in the absence of the eyelid support assembly 100. The lifting of the lower eyelid in this manner may (1) facilitate complete (or more complete) closure of the eyelids, (2) improve the cosmetic appearance of the eye region, and/or (3) reduce the risk and/or occurrence of ectropion, lid laxity, epiphora, lagophthalmos, and/or corneal damage.

FIGS. 2A-2D depict an embodiment of an eyelid support assembly 200 that resembles the eyelid support assembly 100 described above in certain respects. Accordingly, like features are designated with like reference numerals, with the leading digits incremented to "2." For example, the embodiment depicted in FIGS. 2A-2D includes an eyelid support member 230 that may, in some respects, resemble the eyelid support member 130 of FIGS. 1A and 1B. Relevant disclosure set forth above regarding similarly identified features thus may not be repeated hereafter. Moreover, specific features of eyelid support assemblies and related components shown in FIGS. 1A and 1B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the eyelid support assembly 200 and related components depicted in FIGS. 2A-2D. Any suitable combination of the features, and variations of the same, described with respect to the eyelid support assembly 100 and related components illustrated in FIGS. 1A and 1B can be employed with the eyelid support assembly 200 and related components of FIGS. 2A-2D, and vice versa. This pattern of disclosure applies equally to further embodiments depicted in subsequent figures and described hereafter, wherein the leading digits may be further incremented.

Figure 2A:
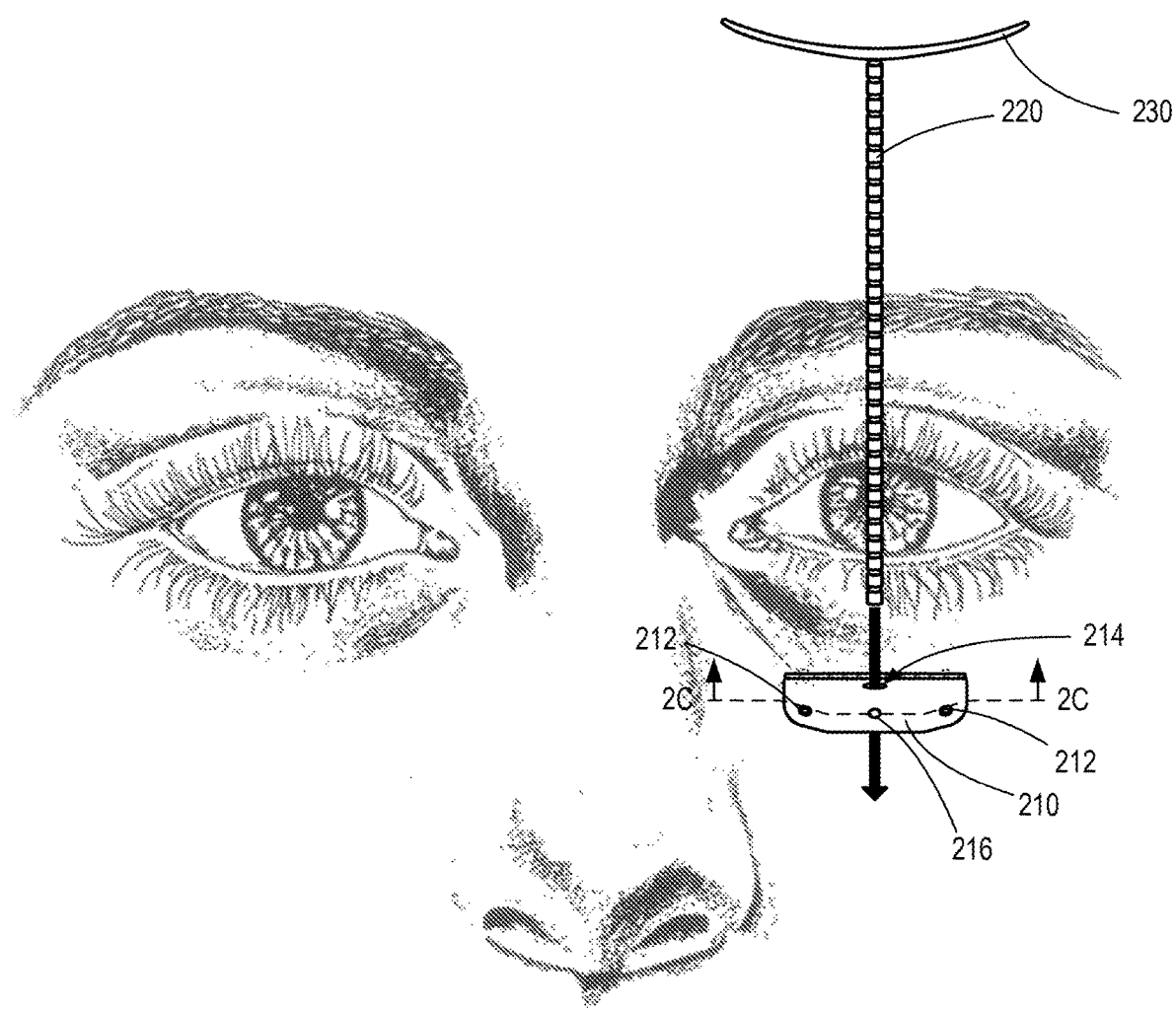
FIG. 2A is a front view of an eyelid support assembly that is configured for adjusting the distance between the mounting plate and the eyelid support member.
Figure 2C:
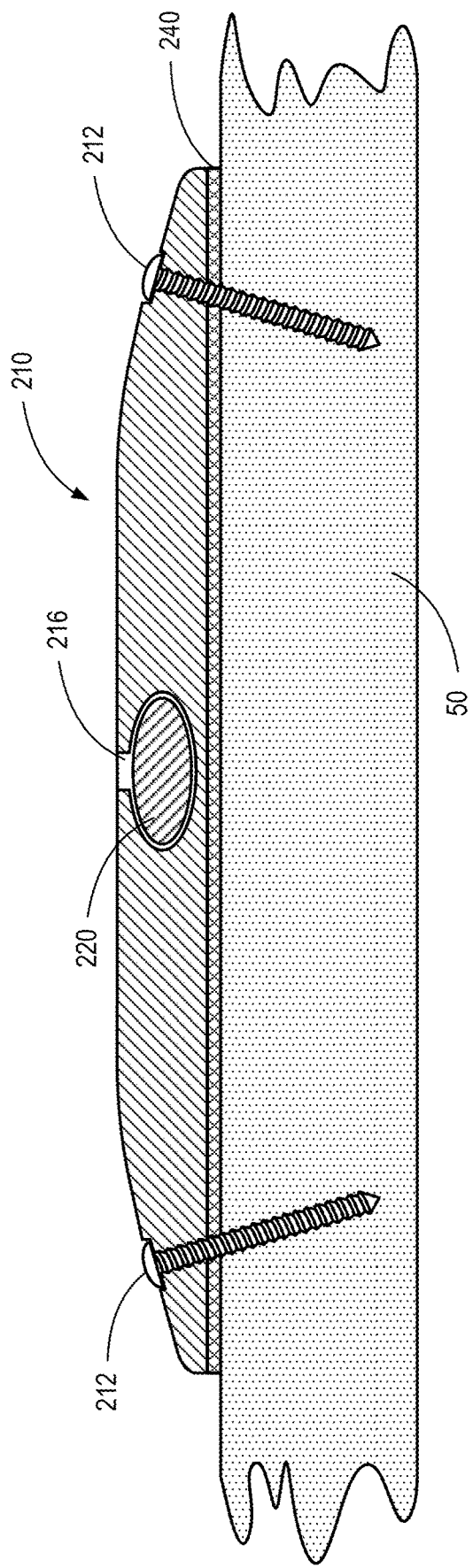
FIG. 2C is a cross-sectional view of the eyelid support assembly of FIG. 2A through line 2C-2C of FIG. 2A.

FIGS. 2A-2D depict an adjustable-length eyelid support assembly 200 (i.e., an eyelid support assembly 200 having a length that may be adjusted by a practitioner). More particularly, FIG. 2A provides a front view of the eyelid support assembly 200 with a mounting plate 210 that is attached to a facial bone 50 of the patient. FIG. 2B provides a front view of the same eyelid support assembly 200, showing the cutting off of a portion of the elongate shaft 220. FIG. 2C provides a cross-sectional view of the eyelid support assembly 200 through line 2C-2C of FIG. 2A. FIG. 2D provides a perspective view of a portion of the eyelid support assembly 200. While the eyelid support assembly 200 is shown with reference to the exterior of a patient's face (i.e., is shown outward relative to the patient's flesh), one of ordinary skill in the art, with the benefit of this disclosure, will recognize that the eyelid support assembly 200 is generally implanted below the skin of a patient.

As depicted in these figures, the eyelid support assembly 200 includes a mounting plate 210, an elongate shaft 220, and an eyelid support member 230. In the depicted embodiment, the elongate shaft 220 and the eyelid support member 230 constitute a single inseparable unit.

In the embodiment depicted in FIGS. 2A-2D, the mounting plate 210 is configured for coupling to a facial bone 50. For instance, in some embodiments, the mounting plate 210 is attached or otherwise coupled to a zygomatic bone of a patient via one or more fasteners 212. Stated differently, fasteners 212, such as bone screws, may extend through the mounting plate 210 and sink into facial bone 50, thereby securing the mounting plate 210 relative to the bone structure of the patient. In some embodiments, the mounting plate 210 is contoured to match the surface of the patient's facial bone 50. In other or further embodiments, the facial bone 50 is shaved to receive the profile of a mounting plate 210. In some embodiments, such as that depicted in FIG. 2A, the mounting plate 210 is attached to the facial bone 50 such that mounting plate 210 is disposed directly below the center of the orbit. In other or further embodiments, the mounting plate is disposed at a position lateral to a center of the patient's eye socket, having an elongate shaft that extends medially from the mounting plate toward the sagittal plane of the patient such that the eyelid support member is disposed directly below the center of the orbit to support the lower eyelid of the patient.

In some embodiments, the mounting plate 210 (e.g., a mounting plate principally made from ultra-high molecular weight polyetheylene) includes a sheet 240 or layer that is configured for contacting facial bone. Stated differently, the sheet 240 may be disposed between a facial bone 50 and the remaining portions of the mounting plate 210. In some embodiments, the sheet 240 is attached (e.g., via an adhesive) to the remaining portion of the mounting plate. In other or further embodiments, the sheet 240 is held against the remaining portion of mounting plate 210 via one or more fasteners 212. In some embodiments, the sheet 240 is a mesh layer or a layer formed by sputter coating. In other or further embodiments, the sheet 240 comprises and/or consists essentially of titanium. For example, in some embodiments, an uneven (rough) titanium layer (e.g., a titanium mesh sheet or applied coating of titanium) may contact facial bone 50 to facilitate bone growth and/or bonding to the sheet 240. Other embodiments (e.g., embodiments in which a titanium mounting plate includes a textured lower surface) may lack a sheet analogous to the sheet 240.

In the depicted embodiment, the mounting plate 210 comprises a channel 214. The channel 214 may run perpendicular to a longitudinal axis of the mounting plate 210. The channel 214 may also be sized and shaped to receive a bottom portion of the elongate shaft 220. Stated differently, the channel 214 may be configured to allow a bottom portion of the elongate shaft 220 to pass through the channel 214. In the depicted embodiment, the channel 214 and the elongate shaft 220 both include cross-sections that are substantially oval in shape. The oblong cross-sectional shapes of the channel 214 and the elongate shaft 220 prevent the elongate shaft 220 from rotating within the channel 214. One of ordinary skill in the art, with the benefit of this disclosure, will recognize that channels and elongate shafts of different shapes and sizes (e.g., channels and shafts with circular or rectangular cross sections) are also suitable for use and within the scope of this disclosure.

When implanting the eyelid support assembly 200, the practitioner may first secure the mounting plate 210 by attaching or otherwise coupling the mounting plate 210 to a facial bone 50 of the patient. For example, in some circumstances, the practitioner may attach the mounting plate 210 to a zygomatic bone of the patient. The practitioner may then thread the bottom portion of the elongate shaft 220 through the channel 214 of the mounting plate 210. As a first (i.e., bottom) end of the elongate shaft 220 is advanced (e.g., slid) through the channel 214, the distance between the mounting plate 210 and a second end of the elongate shaft 220 decreases. Thus, by varying the degree to which the elongate shaft 220 is advanced through the channel 214, the practitioner can adjust the distance between the mounting plate 210 and the second end of the elongate shaft 220. Such adjustment may be accomplished while implanting the eyelid support assembly 200 in a patient. In this manner, a practitioner can adjust the position of an eyelid support member 230 that is coupled to the elongate shaft 220 relative to the mounting plate 210. Stated differently, the adjustable eyelid support assembly 200 may be adjusted to ensure that an eyelid support member 230 is properly positioned to support an eyelid in a manner that takes into account the specific structure of the patient's face.

For instance, an elongate shaft 220 with a second end that is coupled to an eyelid support member 230 may be inserted through a channel 214 of the mounting plate 210 until the eyelid support member 230 is disposed adjacent (e.g., directly below) the inferior tarsus of the patient. In some circumstances, the practitioner may then suture or otherwise couple the eyelid support member 230 to the inferior tarsus. The practitioner may then adjust the position of the eyelid support member 230 (e.g., to lift the eyelid) by moving the elongate shaft 220 relative to the mounting plate 210. Once the elongate shaft 220 has been positioned within the mounting plate 210 such that the second end of the elongate shaft 220 is placed a proper distance from the mounting plate 210, the elongate shaft 220 may be secured relative to the mounting plate 210. For example, an adhesive 5 (e.g., cyanoacrylate glue) may be delivered through a port 216 of the mounting plate 210 (see FIG. 2D) to secure the elongate shaft 220 relative to the mounting plate.

Delivery of an adhesive 5 to secure the elongate shaft 220 relative to the mounting plate 210 may be facilitated by one or more grooves of the elongate shaft 220. For example, in some embodiments, the elongate shaft 220 may comprise one or more grooves 222 that run perpendicular to the longitudinal axis of the elongate shaft 220. Upon delivery of an adhesive 5 through the port 216, the adhesive 5 may flow around the grooves 220. By flowing around the grooves 220, the adhesive 5 may thus extend around the perimeter (e.g., circumference) of the elongate shaft 220 and permanently bond the elongate shaft 220 to the mounting plate 210.

Once the elongate shaft 220 has been properly positioned relative to the mounting plate 210 and secured to the mounting plate 210, any portion of the elongate shaft 220 that has passed through the entire mounting plate 210 (e.g., the first end of the elongate shaft 220) may be cut off and discarded (see FIG. 2B).

When the elongate shaft 220 is positioned within and bonded to (or otherwise fixedly coupled to) the mounting plate 210, the elongate shaft 220 may extend along a path that is substantially equidistant from the sagittal plane of the patient at all points along the path. Stated differently, the elongate shaft 220 may run substantially parallel to the sagittal plane of the patient.

FIGS. 3A-3C depict an eyelid support assembly 300 or components thereof according to another embodiment. More particularly, FIG. 3A provides a cross-sectional view of the eyelid support assembly 300. FIG. 3B provides a bottom view of a first portion 311 of the mounting plate 310 shown in FIG. 3A. And FIG. 3C provides a top view of a second portion 319 of the same mounting plate 310. In the depicted embodiment, the first portion 311 is disposed generally above the second portion 319 when the mounting plate 310 is viewed as shown in FIG. 3A. Stated differently, when the mounting plate 310 is coupled to the facial bone 50, the second portion 319 of the mounting plate 310 may be disposed closer to the facial bone 50 than the first portion 311 of the mounting plate 310. In other words, when the mounting plate 310 is coupled to the facial bone 50, the distance between the first portion 311 of the mounting plate 310 and the facial bone 50 may be greater than the distance between the second portion 319 of the mounting plate 310 and the facial bone 50.

The eyelid support assembly 300 includes a mounting plate 310, an elongate shaft 320, and an eyelid support member 330 (not shown). As noted above, the mounting plate 310 of the eyelid support assembly 300 includes two distinct components: a first portion 311 and a second portion 319. In some embodiments, one or more of the first portion 311 and the second portion 319 comprise or consist essentially of titanium.

In the depicted embodiment, the second portion 319 of the mounting plate 310 includes an aperture 360 that runs adjacent to and along a portion of the length of an elongate shaft 320 that is disposed within the second portion 319 of the mounting plate 310.

The first portion 311 of the mounting plate 310 may include a compression bar 350 that extends from the remainder of the first portion 311 (see FIGS. 3A and 3B). The compression bar 350 may comprise or consist essentially of titanium. Further, in some embodiments, the compression bar 350 includes a plurality of grooves. The compression bar 350 may be sized and shaped to extend through the aperture 360 of the second portion 319 of the mounting plate 310 to engage with the elongate shaft 320.

For instance, as the fasteners 312 are advanced into the facial bone 50, the fasteners may draw the first portion 311 of the mounting plate 310 toward the patient's facial bone 50. By drawing the first portion 311 of the mounting plate 310 toward the patient's facial bone 50, the compression bar 350 may extend through the aperture 360 to engage with and/or compress the elongate shaft 320. Engagement with and/or compression of the elongate shaft 320 by the compression bar 350 may restrict movement of the elongate shaft 320 within the channel 314. Stated differently, advancement of the fasteners 312 into the facial bone may promote frictional engagement of the compression bar 350 with the elongate shaft 320, thereby preventing movement of the elongate shaft 320 through the channel 314.

While the depicted embodiment includes only a single compression bar 350, other embodiments may include a plurality of compression bars that are configured to extend through one or more apertures of a lower plate to engage with the elongate shaft.

Figure 4A:
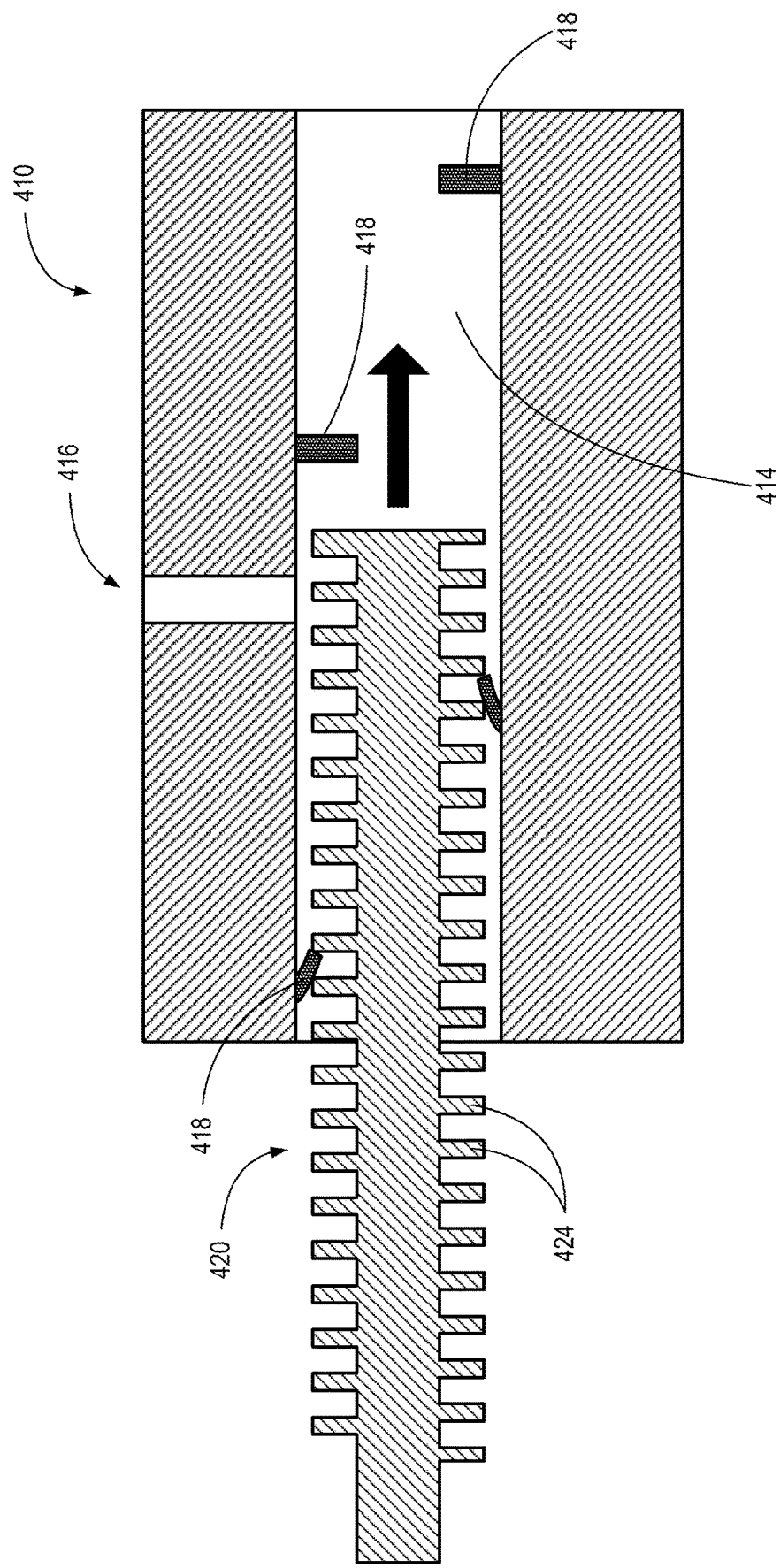
FIG. 4A is a cross-sectional view of an eyelid support assembly wherein the elongate shaft is being inserted into the mounting plate.
Figure 4B:
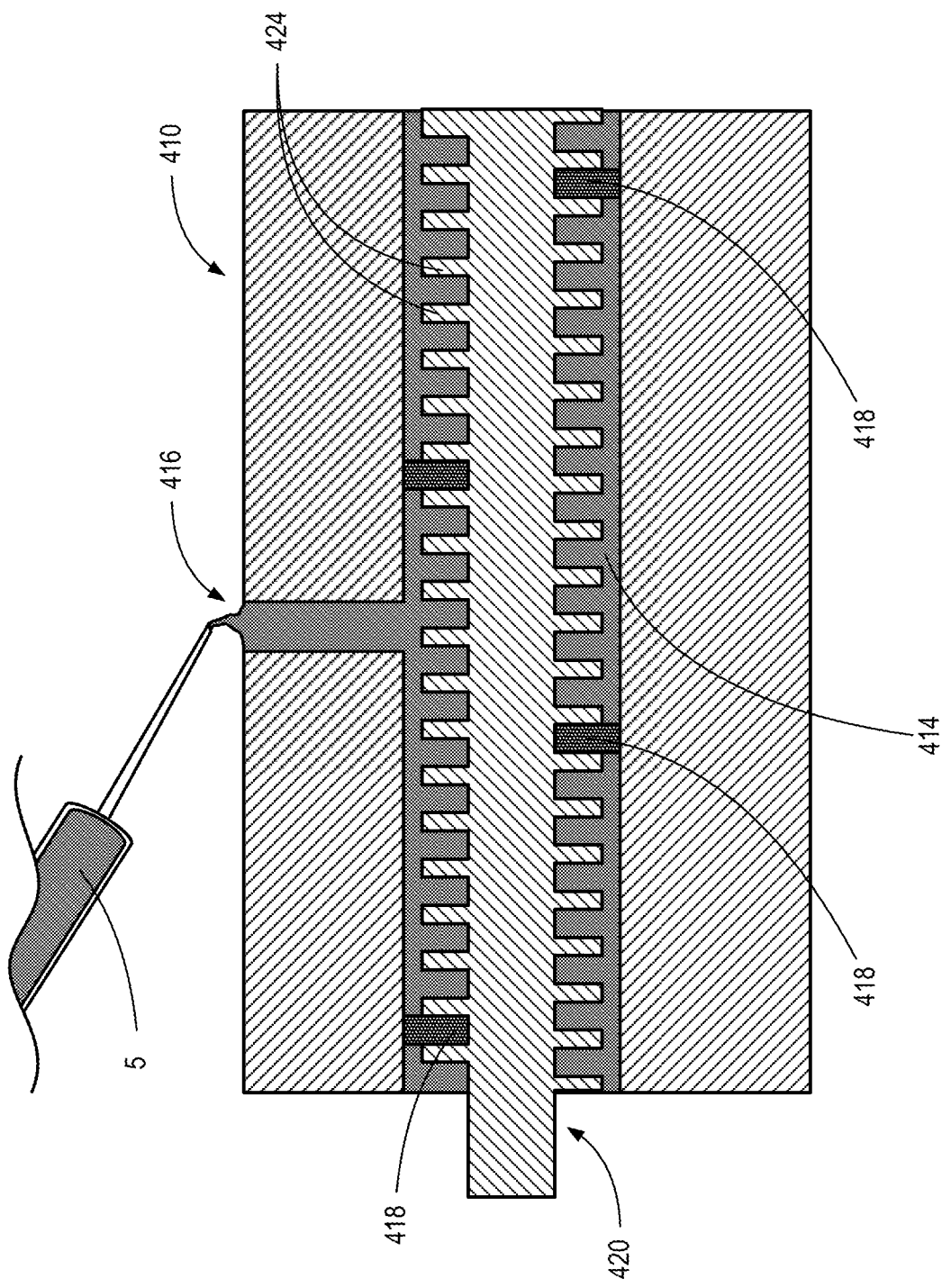
FIG. 4B is a cross-sectional view of the eyelid support assembly of FIG. 4A, depicting the delivery of an adhesive to fasten the elongate shaft to the mounting plate.

FIGS. 4A and 4B provide cross-sectional views of an elongate shaft 420 and a mounting plate 410 of another eyelid support assembly. More particularly, FIG. 4A depicts the insertion of an elongate shaft 420 into mounting plate 410. FIG. 4B depicts the same eyelid support assembly components after the elongate shaft 420 has been properly inserted and adhesive has been added to fixedly secure the elongate shaft 420 relative to the mounting plate 410.

In FIGS. 4A and 4B, the elongate shaft 420 comprises a plurality of protrusions 424 that extend away from the longitudinal axis of the elongate shaft 420. These protrusions 424 form grooves that extend around the elongate shaft 420. The mounting plate 410 also includes a plurality of protrusions 418 that extend into the channel 414 of the mounting plate 410.

As depicted in FIG. 4A, the elongate shaft 420 may be inserted into the mounting plate 410. The protrusions 418 of the mounting plate 410 may deflect as the elongate shaft 420 is advanced within the mounting plate 410, thereby permitting the elongate shaft 420 to advance within the channel 414. Stated differently, as the elongate shaft 420 is inserted into the mounting plate 410, the protrusions 424 of the elongate shaft 420 may contact and deflect the protrusions 418 of the mounting plate 410. The protrusions 418 of the mounting plate 410 may be configured to deflect in one direction to allow the elongate shaft 420 to enter, yet nonetheless prevent deflection in the opposite direction. In other words, the protrusions 418 may allow insertion of the elongate shaft 420 into the mounting plate 410, but not withdrawal of the elongate shaft 420 from the mounting plate 410. The protrusions 418 may be made from a material that differs from that of the rest of the mounting plate 410. For example, the protrusions 418 may be made from or comprise a material that is more flexible than the material from which the rest of the mounting plate 410 is made.

Once the elongate shaft 420 has been inserted such that the second end of the elongate shaft 420 (i.e., the end of the elongate shaft 420 that is not inserted into the mounting plate 410) is disposed a proper distance from the mounting plate 410, the protrusions 418 of the mounting plate 410 may interlock with the protrusions 424 of the elongate shaft 420, thereby preventing (or otherwise impeding) withdrawal of the elongate shaft 420 from the mounting plate 410.

The elongate shaft 420 may be fixedly secured to the mounting plate 410 to prevent both further insertion and withdrawal of the elongate shaft 420. For example, as depicted in FIG. 4B, an adhesive 5 may be delivered through a port 416 of the mounting plate 410. The adhesive may flow around the elongate shaft 420 and fill any voids between the elongate shaft 420 and the mounting plate 410, thereby fixedly bonding the elongate shaft 420 to the mounting plate 410.

While the protrusions 418 of FIGS. 4A and 4B are described as permitting only insertion (and not withdrawal) of the elongate shaft 420 from the mounting plate, in other embodiments, the protrusions do not prevent withdrawal of the elongate shaft 420 from the mounting plate 410. In other words, in some embodiments, the protrusions 418 allow the elongate shaft 420 to move in both directions.

Figure 5A:
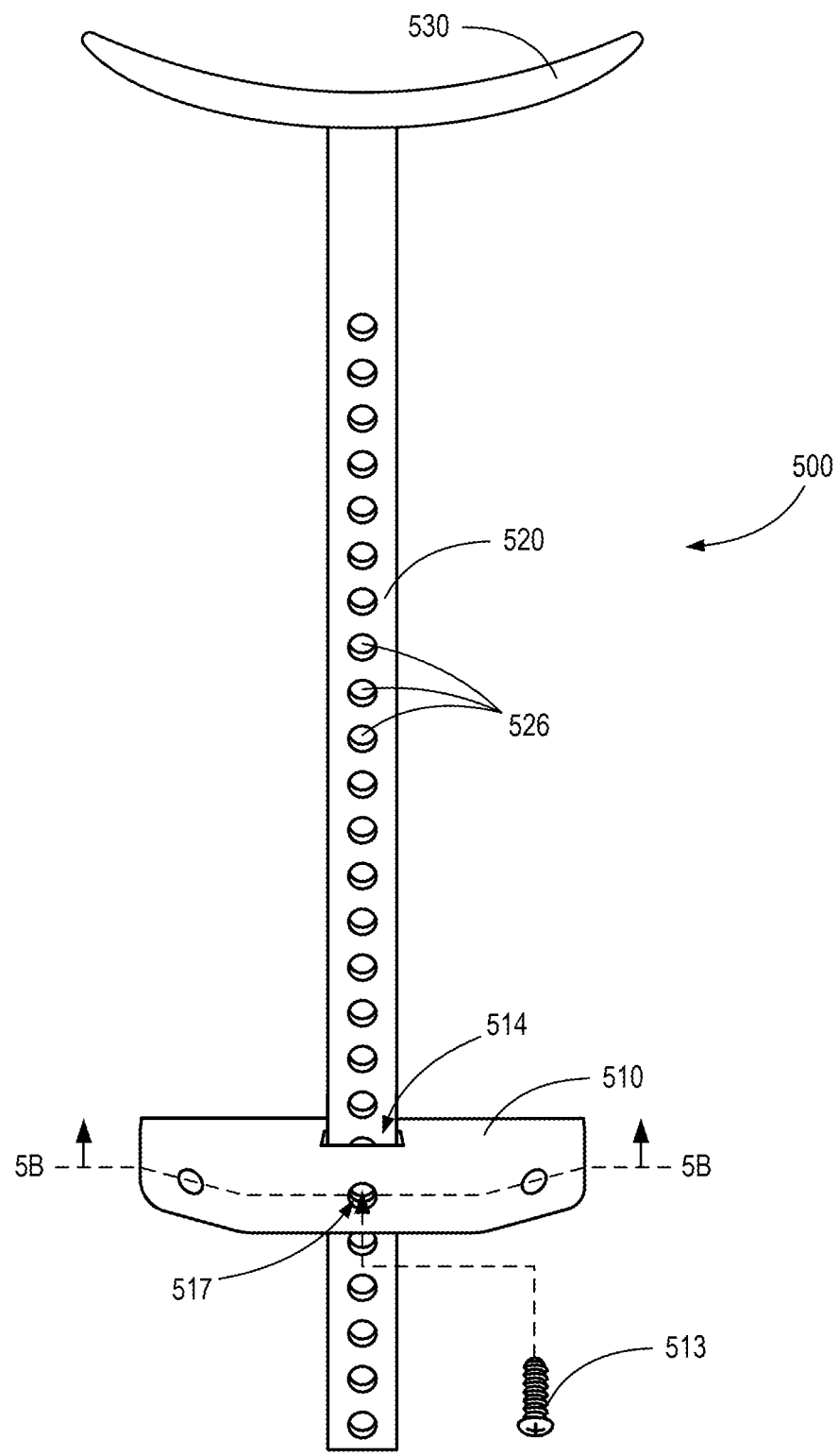
FIG. 5A is a front view of an eyelid support assembly according to another embodiment.
Figure 5B:
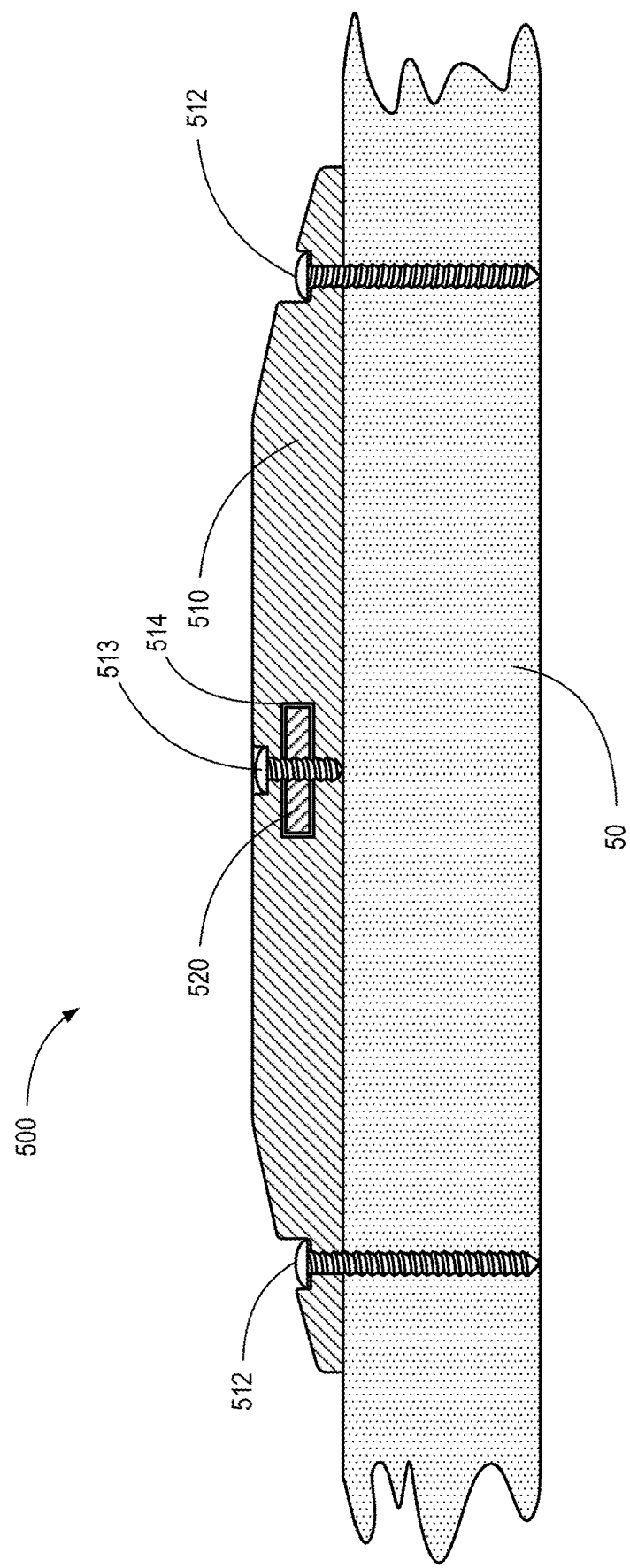
FIG. 5B is a cross-sectional view of the eyelid support assembly of FIG. 5A through line 5B-5B.

FIGS. 5A and 5B depict an eyelid support assembly 500 according to another embodiment. More particularly, FIG. 5A provides a front view of the eyelid support assembly 500, while FIG. 5B provides a cross-sectional view of the eyelid support assembly 500 through line 5B-5B of FIG. 5A. With reference to FIGS. 5A and 5B, the eyelid support assembly 500 may comprise a mounting plate 510, an elongate shaft 520, and an eyelid support member 530.

In the depicted embodiment, the mounting plate 510 is configured for coupling to facial bone 50 of the patient. For example, the mounting plate 510 may be attached to a zygomatic bone, maxilla, or other facial bone of a patient via one or more fasteners 512, such as bone screws. The mounting plate 510 may also comprise a channel 514. The channel 514 may be sized and shaped to receive the elongate shaft 520 of the eyelid support assembly 500. The mounting plate 510 may also comprise a hole 517 for facilitating coupling of the elongate shaft 520 to the mounting plate 510. The hole 517 may be sized and shaped to receive a fastener 513, such as a self-tapping bone screw.

As shown in the depicted embodiment, the elongate shaft 520 includes a plurality of holes 526. The plurality of holes 526 may be aligned along a longitudinal axis of the elongate shaft 520. The elongate shaft 520 may be inserted into the channel 514 of the mounting plate 510 until the elongate shaft 520 is properly positioned for facilitating the support of a lower eyelid. For example, the elongate shaft 520 may be inserted such that an eyelid support member 530 disposed at the second end of the elongate shaft 520 (i.e., the end of the elongate shaft 520 that is not inserted into the channel 514) is positioned to properly lift the lower eyelid of the patient.

Once the elongate shaft 520 has been properly positioned relative to the mounting plate, a hole 517 of the mounting plate 510 may be aligned with one of the plurality of holes 526 of the elongate shaft 520. When these holes are properly aligned, a fastener 513, such as a bonescrew, may be inserted through both the hole 517 and one of the plurality of holes 526 of the elongate shaft 520, thereby fixing the distance between the mounting plate 510 and the eyelid support member 530. Stated differently, the inserted fastener 513 may fixedly attach the mounting plate 510 to the elongate shaft 520, thereby defining the distance from the mounting plate 510 to an eyelid support member 530 that is coupled to the second end of the elongate shaft 520.

FIG. 6 provides a cross-sectional view of an eyelid support assembly 600 according to another embodiment. The eyelid support assembly 600 includes a mounting plate 610, an elongate shaft 620, and an eyelid support member (not shown). In the depicted embodiment, the mounting plate 610 comprises a channel 614 with a cross-section that is rectangular in shape.

The embodiment depicted in FIG. 6 is analogous to the embodiment depicted in FIGS. 5A and 5B, except that the elongate shaft 620 does not include a plurality of holes. The elongate shaft 620 may be inserted into the channel 614 of the mounting plate until the elongate shaft 620 has been inserted to the proper extent. Then a fastener 613, such as a compression screw, may be used to press the elongate shaft 620 against the channel 614 to secure the elongate shaft 620 relative to the mounting plate 610.

FIGS. 7A-7E depict various states of an eyelid support assembly 700, according to another embodiment. As shown in FIGS. 7A-7E, the eyelid support assembly 700 is configured for securing an elongate shaft 720 to a mounting plate 710 via crimping beads 701, 702. The crimping beads 701, 702 may be bands or rings of circular, oval, rectangular, or some other shape that may be compressed to clamp around the elongate shaft 720. For example, as shown in FIG. 7A, a first crimping bead 701 may initially be slipped around a first (i.e., bottom) end of the elongate shaft 720. Then, as shown in FIG. 7B, the bottom end of the elongate shaft 720 may be inserted through a channel of a mounting plate 710 that has been mounted to a facial (e.g., zygomatic) bone of the patient until an eyelid support member 730 that is attached to a second (i.e., top) end of the elongate shaft is disposed adjacent (e.g., directly below) the inferior tarsus of the patient. In some circumstances, the eyelid support member 730 may then be attached (e.g., sutured) to the inferior tarsus. Once the elongate shaft 720 is positioned within the mounting plate 710 such that the eyelid support member 730 is placed a proper distance from the mounting plate 710, the first crimping bead 701 may be compressed at a position that is just above the mounting plate 710. Then, as shown in FIGS. 7C and 7D, a second crimping bead 702 may be placed over the bottom end of the elongate shaft 720 and pushed upward until the second crimping bead 702 is disposed immediately below the mounting plate 710. The second crimping bead 702 may then be compressed, thereby securing the elongate shaft 720 to the mounting plate 710. Once the elongate shaft 720 is secured to the mounting plate 710, the tail of the elongate shaft 720 may be cut off and discarded as shown in FIG. 7E. In some embodiments, the crimping beads 701, 702 may be used in connection with one or more other fasteners. For example, a set screw may also be used to lock the position of the elongate shaft 720 relative to the mounting plate 710.

Figure 8A:
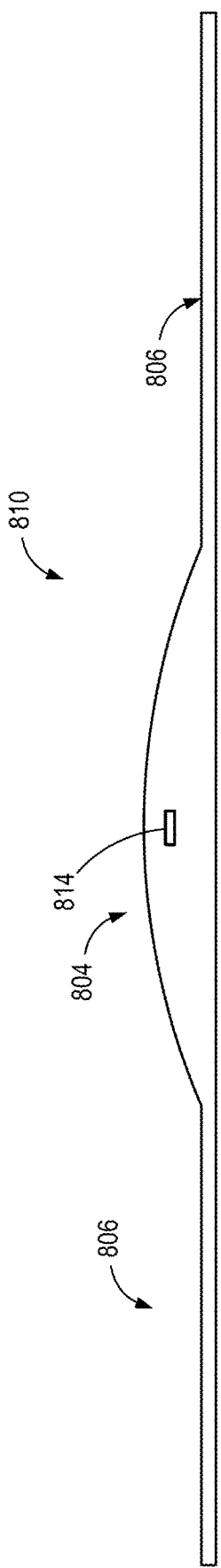
FIG. 8A is a side view of mounting plate.
Figure 8B:
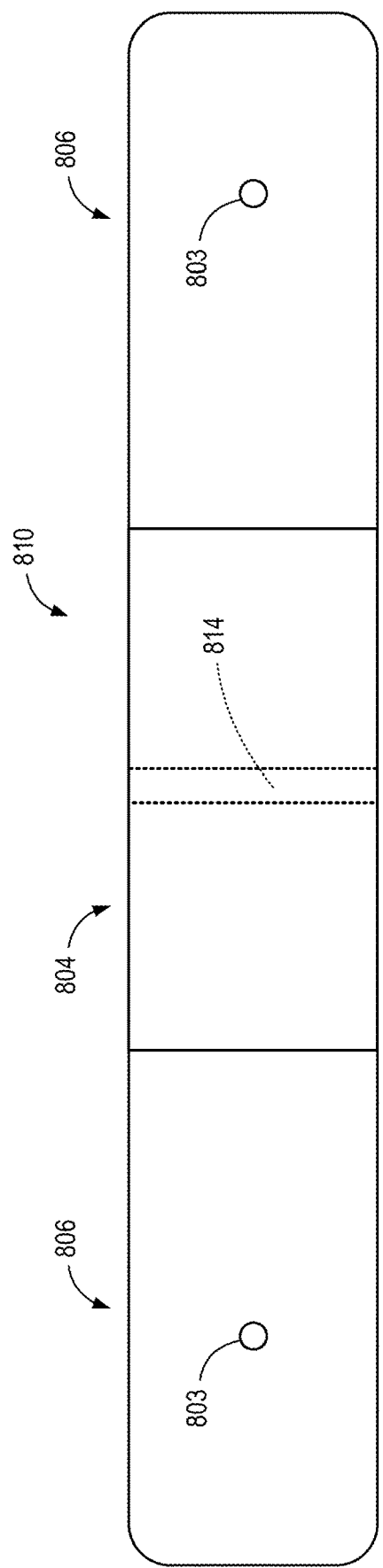
FIG. 8B is a top view of the mounting plate of FIG. 8A.

FIGS. 8A and 8B provide alternative views of a mounting plate 810 for an eyelid support assembly, according to another embodiment. More particularly, FIG. 8A provides a side view of the mounting plate 810, while FIG. 8B provides a top view of the mounting plate 810. The mounting plate 810 is configured for coupling to facial bone, such as the zygomatic bone. For example, the mounting plate 810 may be attached to a zygomatic bone via one or more fasteners that are inserted through apertures 803 in the mounting plate 810. The mounting plate 810 may function as a scaffold to which one or more other elements of an eyelid support assembly may be attached.

In the embodiment depicted in FIGS. 8A and 8B, the mounting plate 810 includes a central region 804 and a pair of lateral regions 806, where the central region 804 is thicker than the lateral regions 806. In some embodiments, the central region 804 gradually rises from the lateral regions 806 to form a relatively smooth hump. The central region 804 may include a channel 814 that is designed to accommodate an elongate shaft. A mounting plate 810 that is designed to have relatively thin lateral regions 806 and a thicker central region 804 may allow for sufficient structure to accommodate an elongate shaft while minimizing the amount of unnecessarily implanted material. The mounting plate 810 may be made from any suitable material (e.g., titanium).

Figure 9:
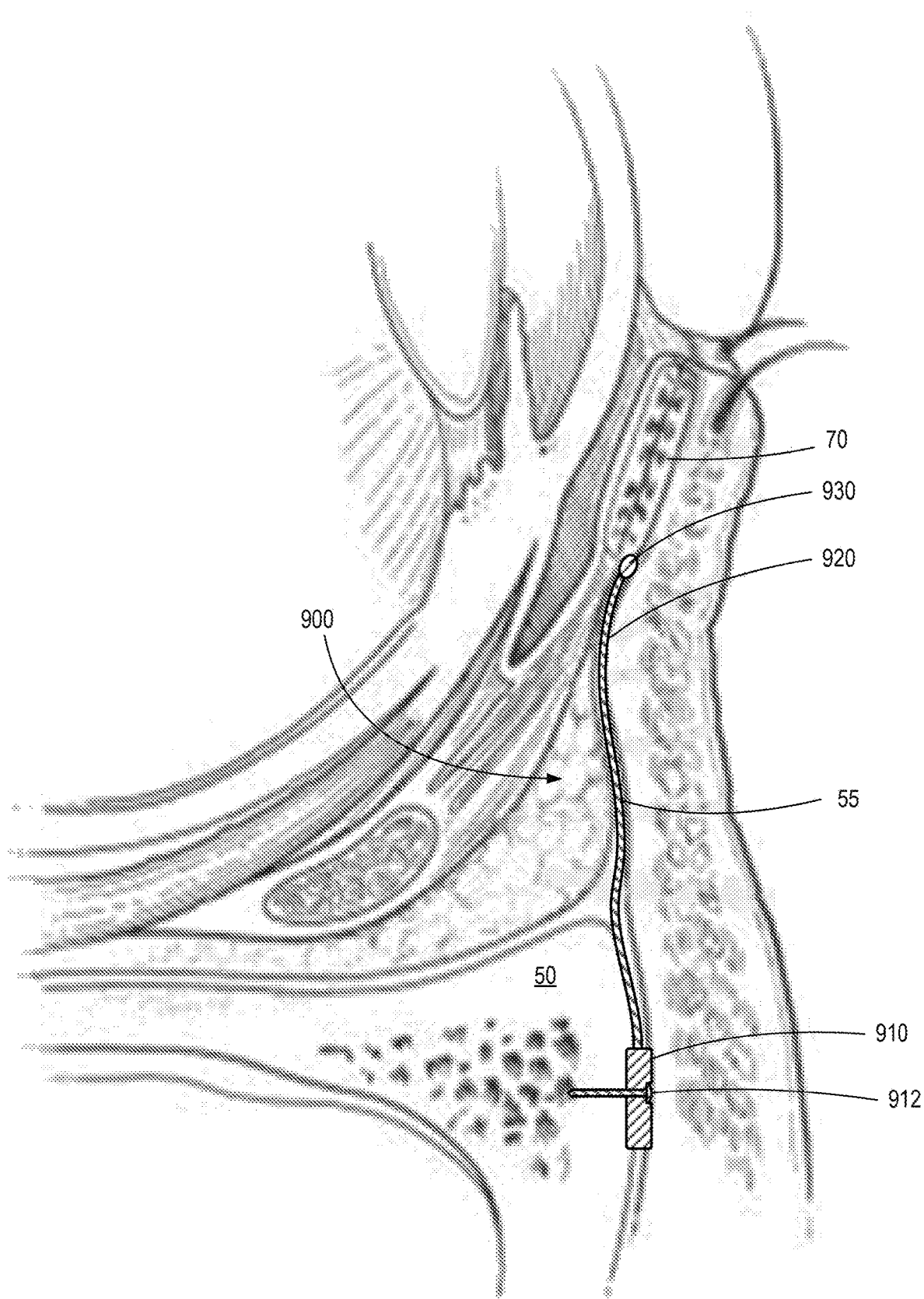
FIG. 9 is partially cut-away side view of an eyelid support member positioned to support an inferior tarsus of a lower eyelid.

FIG. 9 provides a partially cut-away side view of an eyelid support assembly 900 that is positioned to lift a lower eyelid of a patient. The eyelid support assembly 900 includes a mounting plate 910, an elongate shaft 920, and an eyelid support member 930.

As depicted in FIG. 9, the mounting plate 910 is attached to facial bone 50 (e.g., the zygomatic bone) of the patient via one or more fasteners 912. The elongate shaft 920 extends in a generally upward direction from the mounting plate 910. For instance, in some embodiments, the elongate shaft 920 may extend upward from the mounting plate 910 along the orbital septum 55 or nearby anatomy.

The eyelid support member 930 may be attached or otherwise coupled to the second (i.e., top) end of the elongate shaft 920. For example, the support member 930 and elongate shaft 920 may be integrally formed. The elongate shaft 920 may be adjusted by the practitioner to position the eyelid support member 930 such that the eyelid support member 930 lifts the inferior tarsus 70 of the patient. For example, the eyelid support member 930 may be sutured or otherwise attached to the inferior tarsus 70. Accordingly, as the elongate shaft 920 is displaced in a manner that results in lifting the eyelid support member 930, the eyelid support member 930 may lift the inferior tarsus 70 of the patient, thereby providing support to a lower eyelid. Such support may both lift a lower eyelid and/or draw the eyelid toward the patient's eye. In other words, the force supplied by the eyelid support assembly 900 may push the patient's eyelid both upward and inward (i.e., toward the patient's eye).

Figure 10:
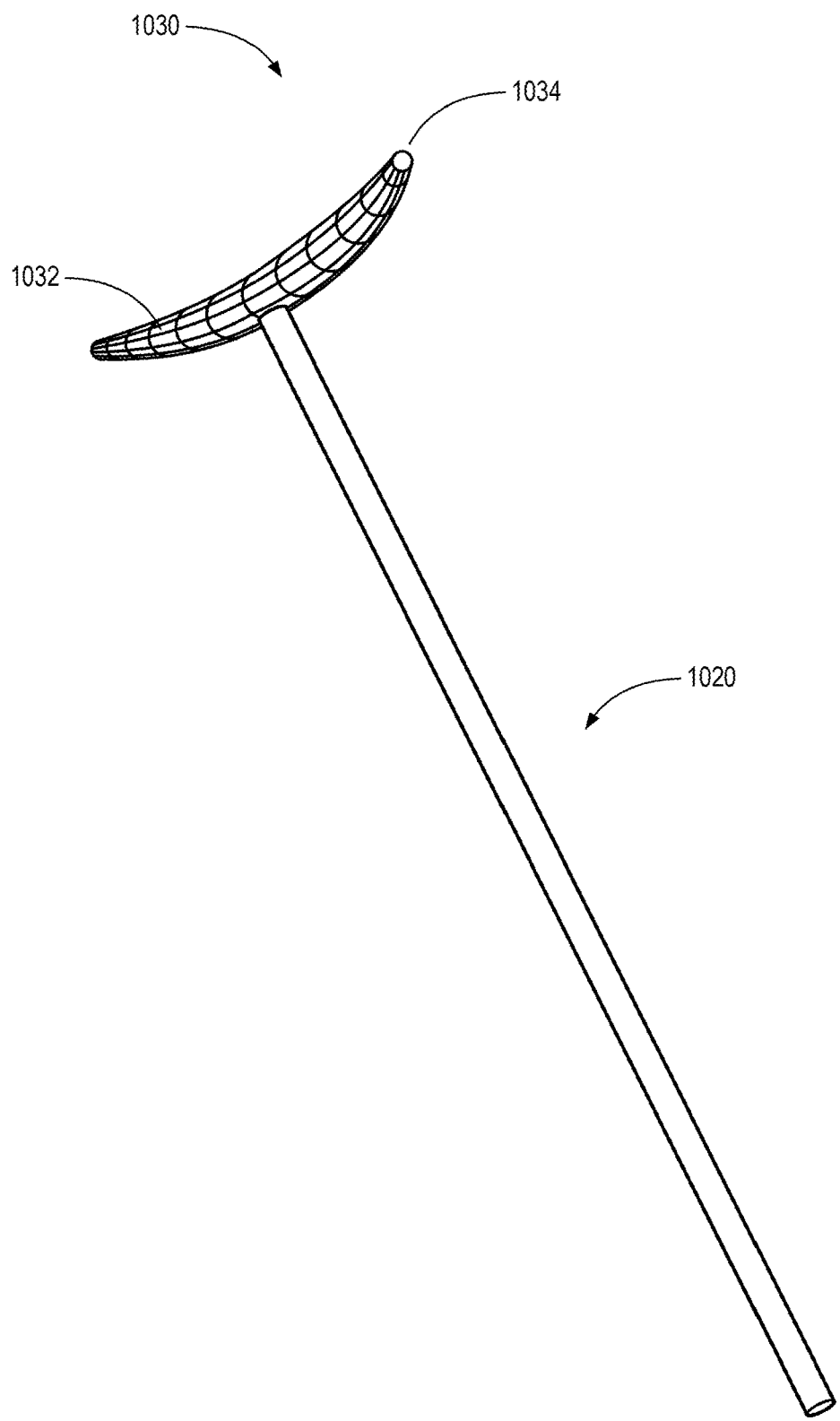
FIG. 10 is a perspective view of an eyelid support member and an elongate shaft of an eyelid support assembly.

FIG. 10 provides a perspective view of a portion of an eyelid support assembly, according to another embodiment. More specifically, FIG. 10 depicts an elongate shaft 1020 that is attached to an eyelid support member 1030.

In the depicted embodiment, the eyelid support member 1030 includes a mesh exterior 1032. The mesh exterior 1032 may substantially define the shape of the eyelid support member 1030. For example, in the depicted embodiment, the mesh exterior of the eyelid support member 1030 is curved in shape. The mesh exterior 1032 may be formed from ultra-high molecular weight polyethylene or any other suitable material.

The eyelid support member 1030 may also include a core interior region 1034. The core interior region 1034 may comprise and/or be filled with biocompatible acellular material derived from skin, such as Alloderm® or other similar materials. Stated differently, the core interior region 1034 may comprise and/or be filled with a collagen-rich matrix. Such material may serve as a scaffold on which living cells of the patient may grow. The use of such material may improve the biocompatibility of the eyelid support assembly. Additionally or alternatively, the use of such material may promote the growth of cells onto the implanted eyelid support member 1030. Such improved growth may promote improved bonding between the eyelid support member 1030 and tissue adjacent the lower eyelid.

Figure 11:
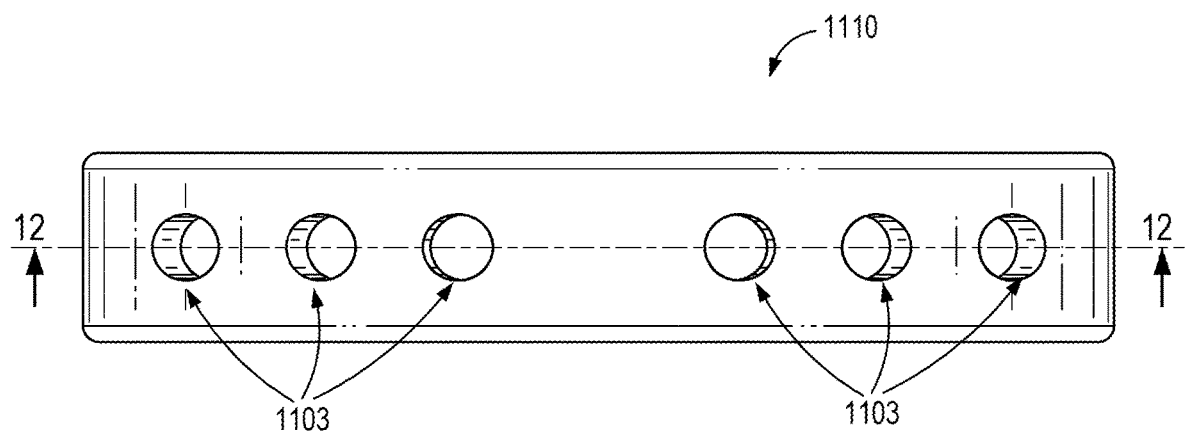
FIG. 11 is a front view of a mounting plate of an eyelid support member according to another embodiment.
Figure 12:
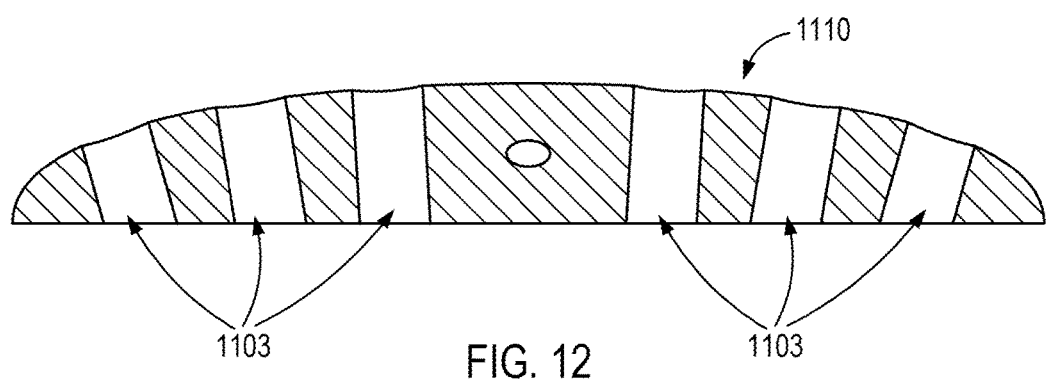
FIG. 12 is a cross-sectional view of the mounting of FIG. 11 through line 12-12.

FIG. 11 provides a front view of a mounting plate 1110 of an eyelid support assembly according to another embodiment. FIG. 12 provides a cross-sectional view of the mounting plate 1110 through the line 12-12 of FIG. 11. The mounting plate 1110 includes a plurality of apertures 1103 that may be used when fastening the mounting plate 1110 to bone of the patient. In some embodiments, the mounting plate 1110 includes one, two, three, four, five, six, or more apertures 1103. Some mounting plates that include a plurality of apertures, such as the mounting plate 1110, may allow a practitioner to select where to place fastener(s) among multiple options. For example, the mounting plate 1110 may be secured to the zygomatic bone of a patient via two screws, one of which is placed in any of the three apertures 1103 on a first side of the center of the mounting plate 1110. The second screw may be placed in any of the three apertures 1103 on the second (i.e., opposite) side of the center of the mounting plate 1110. The practitioner may select where to place each fastener based on the bone density of the patient. For example, the practitioner may choose to place a screw through a hole that is positioned adjacent to bone of sufficient density. As the upper surface of the mounting plate 1110 tapers laterally from the center of the mounting plate 1110, screws placed adjacent the lateral edges of the mounting plate 1110 may extend further into the bone of the patient than screws that are placed adjacent the center of the mounting plate 1110. In some circumstances, more than two fasteners may be used in connecting with mounting plates 1110 that have a plurality of apertures 1103.

Figure 13:
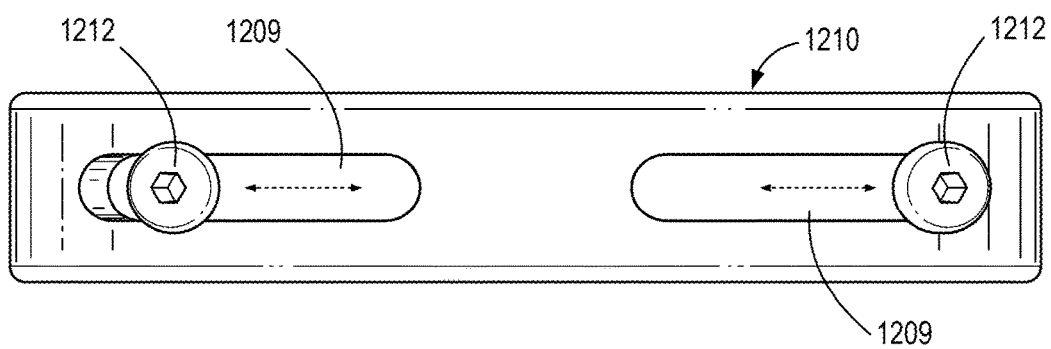
FIG. 13 is a font view of a mounting plate of any eyelid support member according to another embodiment.

FIG. 13 provides a front view of a mounting plate 1210 according to another embodiment. The mounting plate 1210 includes at least one lateral channel 1209 that allows for adjustable placement of fastener(s) 1212. For example, the mounting plate 1210 includes two lateral channels 1209. A first fastener 1212 (e.g., a screw) may be placed at any position along the length of one of the lateral channels 1209. A second fastener 1212 (e.g., a screw) may be placed at any position along the length of the other lateral channel 1209. The practitioner may determine placement of the fasteners 1212 based on the bone density of the patient. Stated differently, the practitioner may place the fasteners 1212 at positions along the lateral channel 1209 where the bone of the patient is sufficiently dense. In some embodiments, the upper surface of the mounting plate 1210 may taper laterally from the center of the mounting plate 1210. Thus, fasteners 1212 placed adjacent the lateral edges of the mounting plate 1210 may extend further into the bone of the patient than fasteners 1212 that are placed adjacent the center of the mounting plate 1210. In some embodiments and/or circumstances, more than two fasteners 1212 may be used in connection with mounting plates 1210 that have lateral channels 1209.

EXAMPLES

The following example is illustrative of disclosed methods and compositions. In light of this disclosure, those of skill in the art will recognize that variations of this example and other examples of the disclosed methods and compositions would be possible without undue experimentation.

Example 1—Stability Analysis of Eyelid Assembly Components and Connections (Accelerated Life Testing)

To test the stability of eyelid support assembly components, along with the connections between these components, a 3×1×25 mm elongate shaft was attached to a 4×4×3 mm mounting plate using a cyanoacrylate glue which was delivered through a 1×3 mm port of the mounting plate. After the cyanoacrylate glue had dried, the mounting plate was immobilized. The end of the elongate shaft disposed opposite the immobilized mounting plate was then deflected laterally from the resting position a distance of 4 mm in both directions at a rate of 30 cycles/minute. The mounting plate, the elongate shaft, and the connection between the mounting plate and the elongate shaft were examined at 8 (14,400 cycles), 16 (28,800 cycles), 24 (43,200 cycles), and 48 hours (86,400 cycles). Both the mounting plate and the elongate shaft survived the entire testing period without noticeable damage. The cyanoacrylate bond between the elongate shaft and the mounting plate likewise survived the entire testing period. There was no observable damage to the glued joint.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. An assembly for lifting a lower eyelid, the assembly comprising:
a mounting plate configured for coupling to a facial bone;
an eyelid support member; and
an elongate shaft configured to extend between and couple the mounting plate to the eyelid support member,
wherein the eyelid support member is curved and configured to follow a contour of an inferior tarsus of a patient, and
wherein the assembly is configured to allow adjustment of a distance between the mounting plate and the eyelid support member as the assembly is implanted into a patient and the distance remains fixed after implantation.

2. The assembly of claim 1, wherein the eyelid support member is configured to contact and lift up an inferior tarsus.

3. The assembly of claim 1, wherein the elongate shaft is attached to the mounting plate.

4. The assembly of claim 1, wherein the mounting plate, the eyelid support member, and the elongate shaft are integrally formed.

5. The assembly of claim 1, wherein prior to securement of the elongate shaft relative to the mounting plate, the elongate shaft is configured to slide within a channel in the mounting plate.

6. The assembly of claim 1, wherein:
the eyelid support member and the mounting plate are both coupled to the elongate shaft; and
when the assembly is implanted into the patient, the elongate shaft extends along a path that is substantially equidistant from a sagittal plane of the patient at all points along the path.

7. The assembly of claim 1, wherein the mounting plate comprises a port for receiving an adhesive.

8. The assembly of claim 1, wherein the elongate shaft is coupled to the mounting plate via one or more compressible bands or crimping beads.

9. The assembly of claim 1, wherein the eyelid support member is configured to be attached to the inferior tarsus of the patient.

10. The assembly of claim 9, wherein the eyelid support member is configured to be attached to the inferior tarsus of the patient via one or more sutures.

11. The apparatus of claim 1, wherein the eyelid support member comprises a core interior region.

12. The apparatus of claim 11, wherein the core interior region comprises biocompatible acellular material.

13. The apparatus of claim 1, wherein the mounting plate extends laterally from the elongate shaft.

14. An assembly for lifting a lower eyelid, the assembly comprising:
a mounting plate configured for coupling to a facial bone;
an eyelid support member; and an elongate shaft configured to extend between and couple the mounting plate to the eyelid support member, wherein the assembly is configured to allow adjustment of a distance between the mounting plate and the eyelid support member as the assembly is implanted into a patient and the distance remains fixed after implantation.

* * * * *